United States Patent [19]

Nordenström

[11] Patent Number: 4,974,595
[45] Date of Patent: Dec. 4, 1990

[54] ELECTRODE DEVICE INTENDED TO BE INTRODUCED INTO THE BODY OF A LIVING BEING

[76] Inventor: Björn Nordenström, Barrtorpsvägen 9, S-144 00, Rönninge, Sweden

[21] Appl. No.: 272,236

[22] Filed: Nov. 14, 1988

[30] Foreign Application Priority Data

Nov. 13, 1987 [SE] Sweden .................. 8704458

[51] Int. Cl.⁵ .................................. A61B 5/04
[52] U.S. Cl. .............................. 128/642; 128/784
[58] Field of Search ............... 128/642, 783, 785, 784, 128/786, 419 P

[56] References Cited

U.S. PATENT DOCUMENTS

| | | | |
|---|---|---|---|
| 3,472,234 | 8/1967 | Tachick | 128/419 P |
| 4,000,745 | 1/1977 | Goldberg | 128/419 P |
| 4,360,031 | 11/1982 | White | 128/786 |
| 4,565,200 | 1/1986 | Cosman | 128/642 |
| 4,572,214 | 2/1986 | Nordenström et al. | 128/785 |

FOREIGN PATENT DOCUMENTS 3038885  5/1982  Fed. Rep. of Germany .
3516830 11/1986  Fed. Rep. of Germany .
81/02839  4/1981  PCT Int'l Appl. .
85/02779 12/1984  PCT Int'l Appl. .
 422885  4/1982  Sweden .

Primary Examiner—Lee S. Cohen
Assistant Examiner—Scott M. Getzow
Attorney, Agent, or Firm—Frishauf, Holtz, Goodman and Woodward

[57] ABSTRACT

An electrode device intended to be temporarily introduced into the body of a living being and to essentially locally treat or electrically measure biological body tissue therein in order to, after a performed treatment or measurement, be removed. The electrode device includes an electrode part (1), provided with an opening to its center and insertable into the body tissue to be treated or measured, and a supply part (2), which is electrically isolated from the remaining body parts, for supply of electricity to the electrode part (1). The supply part (2) is made pliable and contains at least one channel. The electrode part (1) has an unlimited number of openings to its center, which openings preferably are evenly distributed along the entire length of the electrode part (1).

14 Claims, 2 Drawing Sheets

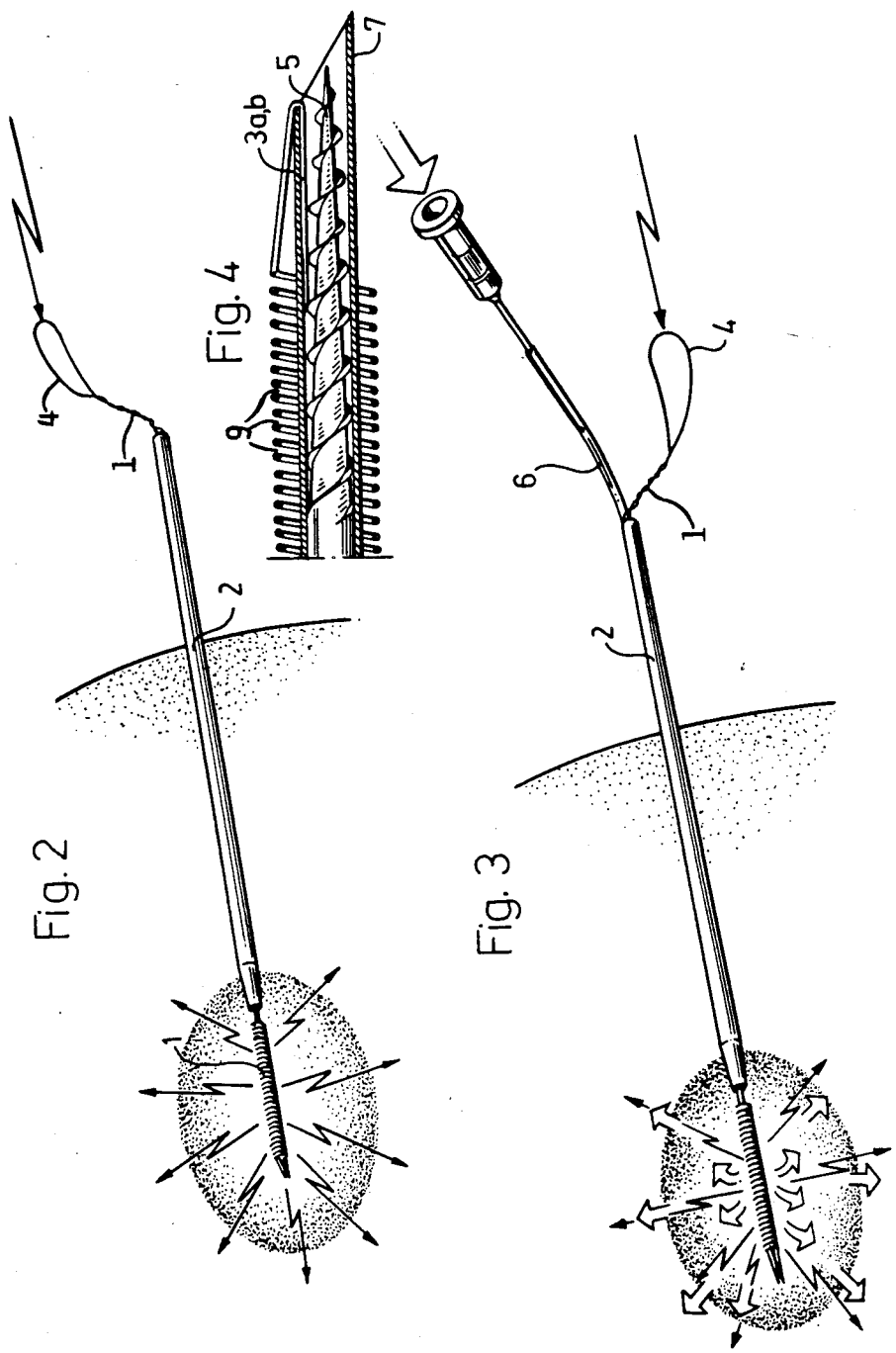

ELECTRODE DEVICE INTENDED TO BE INTRODUCED INTO THE BODY OF A LIVING BEING

BACKGROUND OF THE INVENTION

This invention relates to an electrode device intended to be temporarily introduced into a body of a living being to locally treat or electrically measure biological body tissue therein. After performing the treatment or measurement, the device is removed from the body.

Swedish Patent No. 8002772-5 discloses a prior art electrode device for treatment of biological tissues inside a living being. This known electrode device must—before introduction into the body—be adapted in size by adding one or more electrode rings in order to adapt the extension of the electrode to the size required.

The known electrode device of Swedish Patent No. 8002772-5 is, furthermore, provided with relatively small openings for supply of various agents via its central channel to the point of treatment and for removal of, for example, reaction products from the point of treatment. These openings and the central channel are also utilized for supply to as well as removal from the point of treatment. This makes a simultaneous supply and removal difficult or impossible to perform, for example in order to provide efficient cooling of the point of treatment.

The object of the present invention is to provide an electrode device which is more efficiently adaptable to the size required, preferably in situ at the point of treatment, and which electrode device provides improved transportation to and from the point of treatment and provides an enlarged effective electrode surface compared to previously known techniques.

BRIEF DESCRIPTION OF THE DRAWINGS

FIG. 2 shows an electrode device according to the present invention during local treatment with electricity in situ in a living being;

FIG. 3 shows the same device as shown in FIG. 2 but supplemented with an additional channel for transportation of liquids and/or gases to and from and for cooling of the point of treatment, respectively; and FIG. 4 shows a sectional view through the distal end of the electrode device of the present invention.

DETAILED DESCRIPTION

Figure 1:
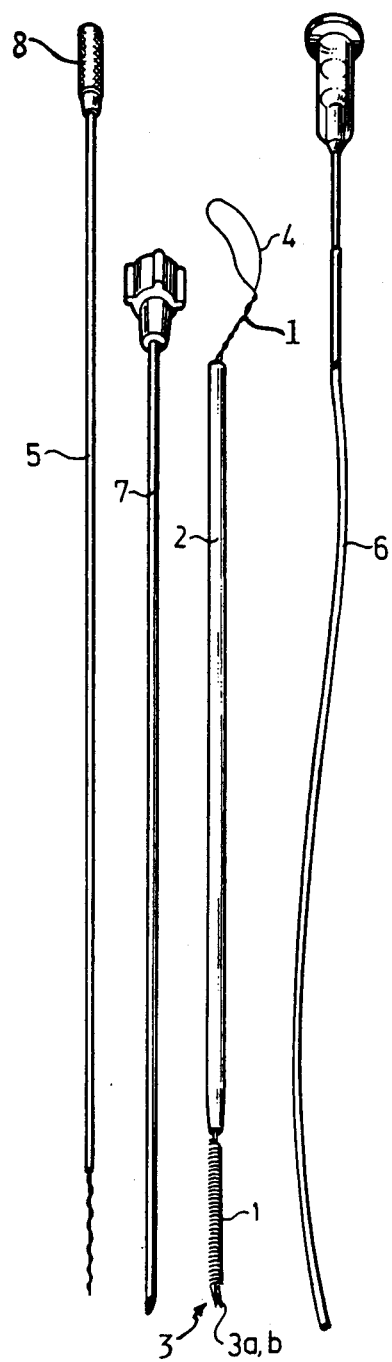
FIG. 1 shows the various parts which can be used when using the electrode device according to the present invention.

As seen in FIG. 1, the electrode part 1 according to the present invention includes one wire which at one end 3a, 3b thereof preferably is bifilar wound. The wire of electrode 1 is preferably made of platinum. The distal ends 3a, 3b of the wire are bent backwards, as is best shown in FIG. 4. The electrode wire runs through an electrically insulated tube 2, made of Teflon (trade name), for example, and the other end 4 of the wire runs through and projects out of the tube 2 and is terminated by a loop. The wire 1 as well as the tube 2 are very flexible and can be bent. Thus, they are difficult or impossible to introduce into a living being.

In order to perform introduction of the electrode device into a living being, a cannula 7 comprising, for example, a stiff steel tube with an obliquely bevelled tip is inserted into the tube 2 and extends to the distal ends 3a, 3b of said wire, as seen in FIG. 4. The distal ends 3a, 3b of the wire are arranged so as to extend into the channel of said cannula 7 by a certain distance, as is best seen in FIG. 4. Furthermore, a screw means 5 having a threaded tip (see FIGS. 1 and 4) is introduced into the channel of said cannula 7 and is turned by means of its handle 8 such that the threaded tip cooperates with said distal ends against the inner wall of said cannula 7, whereby the electrode wire 1 is clamped at the distal ends 3a, 3b thereof in relation to the cannula 7 as well as to the screw means 5.

The assembled unit as described above has become a stiff unit due to the insertion of cannula 7 and screw means 5, and can, thus, be inserted into a living being to the desired point of treatment. When introduced into the living body, the distal ends 3a, 3b of the wire 1 are located at the desired position and the effective length of the electrode part 1 at the point of treatment is adapted to the desired size by pulling the loop-shaped end 4 of the electrode wire outside said living body while the distal ends 3a, 3b are still clamped as specified above. The effective electrode part 1 is, thus, exactly adapted in length to the size desired.

When the above described manipulation has been performed, the screw means 5 can be removed to free the distal ends 3a, 3b by unscrewing said screw means 5. When the screw needle end of screw means 5 is free, the screw needle end is used for pushing out the ends 3a, 3b from the tip of said cannula 7. The screw means 5 can, then, be removed as well as the cannula 7.

The electrode device is now ready to be used, for example, for treatment of the point of treatment with electricity as indicated in FIG. 2. From the point of view of the electrode, the comparatively very large effective electrode surface is to be noted. Furthermore, it is to be noted that the electrode part 1 in itself as well as the electrically insulatng tube 2 are very flexible and pliable and they, thereby, adjust themselves to movements in and around the point of treatment.

Through the tube 2, various agents can be supplied to and removed from the point of treatment. Moreover, communication is taking place via an infinite number of openings 9 (see FIG. 4) distributed around the electrode part 1. As seen in FIG. 4, a continuous opening 9 is provided, which extends around the device along the length of the electrode part 1, which continuous opening 9 is located between the turns of the bifilar wound wire.

The electrode device according to the present invention can—if so desired or required—be supplemented with an extra additional tube or channel 6 (see FIGS. 1 and 3) in the shape of a flexible tube made from, for example, Telfon (trade name), which additional tube or channel 6 is inserted into the channel of said insulating flexible tube 2. Said additional tube or channel 6 can preferably be introduced throughout the whole length of tube 2 and also over a long distance into the electrode part 1, whereby a supply of, for example, cooling agents can be performed through said tube 6 and return transportation can be carried out between the outer wall of said tube 6 and the inner wall of said tube 2. In this manner, a very effective mode of transportation—a circulating transportation—is obtained to and from the point of treatment without any essential obstacles.

When the desired use of the electrode device is completed, the extra channel 6 is firstly removed, whereafter the loop 4 is pulled so that the electrode part 1 is straightened out towards the tube 2 without damaging surrounding tissues, whereafter the tube 2 with the electrode part 1 therein is removed by pulling it out.

I claim:

1. An electrode device for temporary introduction into the body of a living being to substantially locally treat or electrically measure biological body tissue therein, and for removal from the body after a performed treatment or measurement;

the electrode device comprising:

an elongated electrode part (1) having an opening to its center and which is insertable into body tissue to be treated or measured; and a supply part (2) made at least partly of electrically insulating material so as to be electrically isolated from surrounding body parts, for supplying electricity to said elongated electrode part (1), said supply part (2) being pliable and containing at least one channel therethrough;

said elongated electrode part (1) comprising a bifilar wound, screw-shaped cable having a distal end (3) which comprises two wire ends (3a, 3b), which are clamped to the electrode device, and another end which runs through said channel of the isolated supply part (2) and out to the surroundings; and said elongated electrode part (1) being flexible and having a substantially continuous opening (9) to its center, said opening (9) extending around the device and being substantially evenly distributed along substantially the entire length of the elongated electrode part (1).

2. The electrode device of claim 1, wherein said elongated electrode part (1) includes means for varying the size thereof in the longitudinal direction thereof in relation to the body tissue to be treated or measured and relative to said supply part (2), while in situ in the body.

3. The electrode device of claim 2, wherein said two wire ends 3a, 3b, at said distal end (3) comprise a releasable clamp, and wherein said elongated electrode part (1) has a second end (4) which is movable.

4. The electrode device of claim 1, wherein said elongated electrode part (1) includes means for adjusting a longitudinal extension thereof so that it is changeable by adjusting the length thereof.

5. The electrode device of claim 1, wherein said bifilar wound, screw shaped cable comprises a spirally wound wire portion, said substantially continuous opening being defined by spaces between turns of said spirally wound wire portion.

6. The electrode device of claim 1, wherein said elongated electrode part (1) comprises a grip (4) thereon.

7. The electrode device of claim 1, wherein said channel has a cross section sized to permit introduction of an extra channel-forming means therein for defining an extra channel, said extra channel-forming means having a length such that said extra channel can emerge in a desired position in a center portion of said elongated electrode part (1).

8. The electrode device of claim 1, wherein said elongated electrode part (1) comprises a thin wire or thread in order to be pliably straightened out during removal thereof from the body of the living being.

9. An electrode device for temporary introduction into the body of a living being to substantially locally treat or electrically measure biological body tissue therein, and for removal from the body after a performed treatment or measurement;

the electrode device comprising:

an elongated electrode part (1) having an opening to its center and which is insertable into body tissue to be treated or measured; and a supply part (2) made at least partly of electrically insulating material so as to be electrically isolated from surrounding body parts, for supplying electricity to said elongated electrode part (1), said supply part (2) being pliable and containing at least one channel therethrough;

said elongated electrode part (1) being flexible and having a substantially continuous opening (9) to its center, said opening (9) extending around the device and being substantially evenly distributed along substantially the entire length of the elongated electrode part (1); and said channel of said supply part (2) having a cross section sized to permit introduction of an extra channel-forming means therein for defining an extra channel, said extra channel-forming means having a length such that said extra channel can emerge in a desired position in a center portion of said elongated electrode part (1).

10. The electrode device of claim 9, wherein said elongated electrode part (1) includes means for varying the size thereof in the longitudinal direction thereof in relation to the body tissue to be treated or measured and relative to said supply part (2), while in situ in the body.

11. The electrode device of claim 10, wherein said two wire ends 3a, 3b at said distal end (3) comprise a releasable clamp, and wherein said elongated electrode part (1) has a second end (4) which is movable.

12. The electrode device of claim 9, wherein said elongated electrode part (1) includes means for adjusting a longitudinal extension thereof so that it is changeable by adjusting the length thereof.

13. The electrode device of claim 9, wherein said elongated electrode part (1) comprises a grip (4) thereon.

14. The electrode device of claim 9, wherein said elongated electrode part (1) comprises a thin wire or thread in order to be pliably straightened out during removal thereof from the body of the living being.

* * * * *